United States Patent [19]

Hill

[11] Patent Number: 5,525,492
[45] Date of Patent: Jun. 11, 1996

[54] PROCESS FOR AMPLIFYING HLA SEQUENCES

[75] Inventor: Adrian V. S. Hill, Oxford, United Kingdom

[73] Assignee: ISIS Innovation, Ltd., Oxford, United Kingdom

[21] Appl. No.: 50,232

[22] PCT Filed: Nov. 5, 1991

[86] PCT No.: PCT/GB91/01935

§ 371 Date: May 14, 1993

§ 102(e) Date: May 14, 1993

[87] PCT Pub. No.: WO92/07956

PCT Pub. Date: May 14, 1992

[30] Foreign Application Priority Data

Nov. 5, 1990 [GB] United Kingdom ............ 9024005

[51] Int. Cl.⁶ .................. C12P 19/34; C12Q 1/68; C07H 21/04
[52] U.S. Cl. ............... 435/91.2; 435/6; 536/24.3; 536/23.5
[58] Field of Search .......... 435/6, 91.2; 536/24.3, 536/23.5

[56] References Cited

U.S. PATENT DOCUMENTS 5,130,238  7/1992  Malek et al. .................. 435/91.2

FOREIGN PATENT DOCUMENTS

| 0237362 | 9/1987 | European Pat. Off. | .......... C12Q 1/68 |
| 0354580 | 2/1990 | European Pat. Off. | ........ C07H 21/04 |
| 0414469 | 2/1991 | European Pat. Off. | .......... C12Q 1/68 |

OTHER PUBLICATIONS

Choo et al (Human Immunology 21:209–219) 1988.
Weiss et al (Immunobiology 170:367–380) 1985.
The Lancet vol. 337, No. 8742, Mar. 16, 1991, pp. 640–642, Hill et al.
The American Society for Histocompatibility & Immunogenetics, 16th Annual Meeting Abstracts, Nov. 3–7, 1990.

*Primary Examiner*—W. Gary Jones
*Assistant Examiner*—Eggerton Campbell
*Attorney, Agent, or Firm*—Marks & Murase; Michael D. Bednarek

[57] ABSTRACT

The present invention is directed to a process for HLA typing in polymorphic systems by polymerase chain reaction of the nucleic acids. More specifically, the oligonucleotide primers and probes are drawn to the alpha domain of the HLA gene.

10 Claims, 4 Drawing Sheets

FIG. 1 α₁ DOMAIN

```
                  1         10        20        30        40        50        60        70        80        90
CONSENSUS         GSHSMRYFYTSVSRPGRGEPRFIAVGYVDDTQFVRFDSDAASPRMEPRAPWIEQEGPEYWDRETQIVKAQSQTDRESLRTLRGYYNQSEA
B35               -----------------AM-------------------------------T----------------N----F-TNT--Y-----N------------
BSNA              -----------------AM-------------------------------T----------------N----F-TNT--Y-----N------------
B51               -----------------AM-------------------------------T----------------N----F-TNT--Y--N--IALR--------
B51 (W)           -----------------AM-------------------------------T----------------N----F-TNT--Y--N--RLR---------
Bw52              -----------------AM-------------------------------T----------------------S-TNT--Y--N--IALR--------
B ?               -----------------AM-------------------------------T--------------G--RNM--SA--Y--N--IALR--------
Bw58              -----------------AM-------------------------------T--------------G--RNM--SA--Y--N--IALR--------
Bw57              -----------------AM-------------------------------A--------------G--RNM--SA--Y--N--IALR--------
B*2705            -----------------H--------------------------------E--------------------C--KA-------D--LR---------
B*2702            -----------------H--------------------------------E--------------------C--KA-------N--IALR-------
B*2704            -----------------H--------------------------------E--------------------C--KA----------LR---------
B*2706            -----------------H--------------------------------E--------------------C--KA----------LR---------
B*2701            -----------------H--------------------------------E--------------------C--KA--Y--N--ALR---------
B*2703            -----------------H-----------------T--------------E-----------H---------C--KA-------D--LR---------
B44.1             -----------------AM------------T------------------K--------------------S-TNT--Y--N--AAR---------
B44.2             -----------------AM------------T------------------K--------------------S-TNT--Y--N--ALR---------
B13.2             -----------------AM------------T----------A-------K--------------------S-TNT--Y--N--ALR---------
B13.1             -----------------AM------------T----------A-------K--------------------S-TNT--Y--N--ALR---------
Bw47              -----------------AM-------------------------------K--------------------S-TNT--Y--N--ALR---------
B37               -----------------H-----------------S--------------T--------------------S-TNT--Y--D--LR---------
B49               -----------------H-AM----------T------------------T--------------------S-TNT--Y--D--LR---------
B38               ---------------------------S----------------------L--------------------S-TNT--Y--N--IALR-------
B39               -----------------------------S--------------------E-------------N------C-TNT--Y--N--IALR-------
Bw65              -------------A---------------S--------------------E--------------------N-C-TNT-------N----------
B14               ------------------------------S-------------------E--------------------N-C-TNT-------N----------
B18               -----------------H-----------S------C-------------T--------------------N-C-TNT-------N----------
B40*              -----------------H--------------------------------T--------------------N--S-TNT--Y---N----------
Bw41              -----------------H-AM----------T------------------K--------------------S-TNT--Y-------N----------
Bw60              -----------------H-AM----------T------------------K--------------------S-TNT--Y-------N----------
B8                -----------------H-AM----------T------------------K--------------------S-TNT--Y-------N----------
Bw42              -----------------D-AM---------------------------------E--------------N--F-TNT-------N----------
B7.1              --------------------------------S-----------------E---------------------N--Y--A-------N----------
B7.2              --------------------------------S-----------------E---------------------N--Y--A-------N----------
Bw62              -----------------AM-------------S-----------------E---------------------N--Y--A-------N----------
Bw46              -----------------AM-------------------------------A--------------------S-TNT--Y-----V---N----------
CONSENSUS         SHSMRYFYTSVSRPGRGEPRFIAVGYVDDTQFVRFDSDAASPRMEPRAPWIEQEGPEYWDRETQIVKAQSQTDRESLRTLRGYYNQSEA
                  1         10        20        30        40        50        60        70        80        90
```

FIG. 2

α₁ DOMAIN

```
         1         10        20        30        40        50        60        70        80        90
         GSHSMRYFYTSVSRPGRGEPRFIAVGYVDDTQFVRFDSDAASPRMEPRAPWIEQEGPEYWDRETQIVKAQSQTDRESLRTLRGYYNQSEA
Bw53     ********--AM-----------------------------------T----------------N--F-TNT--Y--N--IALR-----
B35      ----------AM-----------------------------------T----------------N--F-TNT--Y--N----------
BSNA     ----------AM-----------------------------------T----------------N--F-TNT--Y--N----------
B51      ----------AM-----------------------------------T----------------N--F-TNT-----N----------
Bw52     ----------AM-----------------------------------T----------------N--F-TNT-----N----------
Bw58     ----------AM-----------------------------------T----------------S-TNT--Y--N--IALR-------
Bw57     ----------AM-----------------------------------------A----------G-RNM--SA--Y--N--IALR----
         ----------AM-----------------------------------------A----------G-RNM--SA--Y--N--IALR----
```

α₂ DOMAIN

```
         100       110       120       130       140       150       160       170       180
         GSHTLQRMYGCDVGPDGRLLRGYHQYAYDGKDYIALNEDLRSWTAADTAAQITQRKWEAARVAEQLRAYLEGTCVEWLRRYLENGKETLQRA
Bw53     ---II----L----------HD-S-------------S--------------------------------L------------------
B35      ---II----L----------HD-S-------------S--------------------------------L------------------
BSNA     ----W-T-------------HN---------------S----------------------E---------L-----H------------
B51      ----W-T-------------HN---------------S----------------------E---------L-----H------------
Bw52     ----W-T-------------HN---------------S----------------------E---------L-----H------------
Bw58     ---II----L----------HD-S---------------------------------------------L-----H------------
Bw57     ---II-V-------------HD-S---------------------------------------------L-------------------
```

α₃ DOMAIN

```
         190       200       210       220       230       240       250       260       270
         DPPKTHVTHHPISDHEATLRCWALGFYPAEITLTWQRDGEDQTQDTELVETRPAGDRTFQKWAAVVVPSGEEQRYTCHVQHEGLPKPLTLRW
Bw53     -----------V******************************************************************************
B35      -----------V*******************************************************************************
BSNA     -----------V*******************************************************************************
B51      -----------V*******************************************************************************
Bw52     -----------V*******************************************************************************
Bw58     -----------V*******************************************************************************
```

FIG. 4

α1 DOMAIN

```
              1         10        20        30        40        50        60        70        80        90
CONSENSUS  GSHSMRYFYTSVSRPGRGEPRFIAVGYVDDTQFVRFDSDAASPRMEPRAPWIEQEGPEYWDRETQIVKAQSQTDRESLRTLRGYYNQSEA
*2701      ------H-------T------------E-------------------------C--KA--Y-N---ALR--------
*2702      ------H-------T------------E-------------------------C--KA----N--IALR--------
*2703      ------H-------T------------E----------H--------------C--KA----D----LR--------
*2704      ------H-------T------------E-------------------------C--KA--------LR--------
*2705      ------H-------T------------E-------------------------C--KA----D----LR--------
*2706      ------H-------T------------E-------------------------C--KA--------LR--------
           PRIMER>                                                       B*2703    B27      <PRIMER
```

FIG. 5

|  |  |  |  |  |  |  |  |  |  |  |  |
|---|---|---|---|---|---|---|---|---|---|---|---|
| 13 | 14 | 15 | 16 | 17 | 18 | 19 | 20 | 21 | 22 | 23 | 24 |
| 1 | 2 | 3 | 4 | 5 | 6 | 7 | 8 | 9 | 10 | 11 | 12 |

PROCESS FOR AMPLIFYING HLA SEQUENCES

This application is a 371 of PCT/GB91/01935, filed on Nov. 5, 1991, which is claiming priority to GB 9024005.2, filed on Nov. 5, 1990.

The present invention relates to a process for amplifying a desired nucleic acid sequence, and in particular for the amplification of a nucleic acid sequence encoding at least part of a human leucocyte antigen.

Human leucocyte antigen (HLA) allele typing has traditionally been performed by serological methods. This involves isolating white blood cells that express human leucocyte antigens on their surface and determining (usually microscopically) whether certain antibodies kill the cells.

Recently nucleic acid amplification techniques such as the polymerase chain reaction (PCR) has been used in combination with Southern blot techniques to type HLA class II alleles. Since there are a large number of cross-hybridising HLA class I sequences restriction fragment length polymorphism analysis has so far failed to distinguish HLA class I alleles and no report of successful HLA class I typing using PCR has appeared.

PCR techniques themselves are known from EP-A-0200362, EP-A-0201184 and EP-A-0258017, all of which are in the name of Cetus Corporation. These publications disclose processes for amplifying a desired nucleic acid sequence by treating separate complementary strands of nucleic acid with a molar excess of two oligonucleotide primers, and extending the primers (often using Klenow fragment) to form complementary primer extension products which act as templates for synthesising the desired nucleic acid sequence. EP-A-0258017 teaches that the use of DMSO in an amplification buffer is undesirable when using a heat stable polymerase such as Taq polymerase as it inhibits the activity of the polymerase, and that the addition of EDTA will halt amplification by inactivating the polymerase.

Although various nucleic amplification techniques are known in the art, successful amplification of a desired sequence will usually depend upon the primers employed to generate the extension products. However, even when the desired sequence is known, and a primer capable of hybridizing to that sequence determined, successful amplification is not guaranteed. Indeed, except within carefully chosen parameters, it is virtually impossible to predict whether a chosen primer will allow amplification. This unpredictability stems from the following two problems associated with amplification.

Firstly, the primer may loop back on itself (to form a hairpin) or form a complex structure, both of which will prevent amplification of the desired sequence.

Secondly, the primer may hybridize to a different sequence from the one that is desired to amplify. (This problem is also encountered when designing probes for a specific sequence.)

These factors contribute to the difficulties encountered with HLA typing.

HLA is the human version of the major histocompatibility complex (MHC) which is a cluster of genes that encode for cell surface antigens on leucocytes. These antigens are responsible for rejection of skin and organ grafts between individuals. Such antigens can be classified into three classes:
1. class I (covering types A, B and C);
2. class II (covering types SB, DC and DR); and
3. class III (covering types C2, C4 and Bf).

The present invention seeks to overcome or at least mitigate some or all of the above problems, and provide a PCR technique that may allow the typing and sub-typing of human leucocyte antigens.

Therefore, according to a first aspect of the present invention there is provided a process for amplifying a nucleic acid sequence comprising two complementary strands (which may or may not be hybridized), at least one strand coding for a human leucocyte antigen (HLA) sequence, the process comprising:

(a) hybridising one oligonucleotide primer to each strand of the nucleic acid sequence to be amplified, each primer being complementary or substantially complementary to a respective strand of the nucleic acid sequence;

(b) synthesising an extension product from each primer in a buffer containing a polar aprotic solvent such as dimethylsulphoxide (DMSO) so that each extension product, when it is separated from its complement, can serve as a template for synthesis of an extension product of the other primer, at least one of the extension products comprising the HLA sequence;

(c) separating the primer extension products from their templates; and (d) synthesising primer extension products from the oligonucleotide primers used in (a) using the single strands produced in (c) as templates.

The present application thus allows HLA sequences and alleles to be grouped into types and sub-types by being able to successfully amplify HLA sequences. The Applicants believe that the very high GC nucleotide content of HLA sequences, especially class I sequences which can be from 70 to 75% GC rich, may be responsible for previously unsuccessful attempts to employ PCR in HLA typing. It is believed that the use of a buffer containing a polar aprotic solvent such as DMSO during amplification allows amplification of such (often GC rich) sequences to be viably repeated. Usually two primers are employed (one specific for each of the two strands of the nucleic acid sequence to be amplified).

The HLA nucleic acid sequence suitably comprises a sequence from the class I, II or III alleles, although class I is the class of choice. The present invention has been found to be particularly useful for amplifying class I sequences as they are often GC rich. Suitable class I sequences include sequences that belong to type A, B or C, and preferably type B.

For efficient amplification it is preferred that the stages (b) to (d) are repeated at least once. Repetition for at least 20, and preferably 30, times is generally preferred.

The stages, (b) and (c) are suitably accomplished by treatment with the four different nucleotide triphosphates and a polymerization agent, such as DNA polymerase I, a Klenow fragment of DNA polymerase I, T4 DNA polymerase or reverse transcriptase. However, the polymerisation agent of choice is a heat-stable enzyme such as a Taq polymerase (available from Cetus Corporation, 1400 53rd Street, Emeryville, Calif. 94608, U.S.A.). Efficient amplification has been achieved with this enzyme despite the fact that EP-A-0258017 teaches that DMSO inhibits its polymerase activity.

The oligonucleotide primers are preferably specific for at least a portion of an alpha domain of the HLA gene, such as alpha 2 or (preferably) alpha 1, suitably found in the HLA B-type. In particular, the primers are preferably less than 30, and more particularly less than 20, nucleotide in length. Suitable primers are those that are specific for at least a portion of the nucleic acid corresponding to any or all of the following regions:

1. residues 1 to 50, such as 1 to 30, and optimally 1 to 10, of the alpha 1 domain;
2. residues 51 to 93, such as 60 to 90, of the alpha 1 domain; or
3. residues 101 to 150, such as 105 to 130, optimally 110 to 125, of the alpha 2 domain.

In this specification, the phrase "corresponding to" means, unless the context requires otherwise, that the nucleic acid codes for, or is complementary to nucleic acid coding for, the amino acids or residues specified.

Thus particularly preferred primers are capable of hybridizing to (and will thus be complementary, or substantially complementary, to) a nucleic acid sequence corresponding to (in the sense of coding for, or being complementary to, nucleic acid coding for) any or all of the the following regions:

(1) residues 2–8 and/or residues 85–90 (which primers can be used to amplify HLA class I alleles, types A, B and C);
(2) residues 2–8 and/or residues 67–72 (which primers can be used to amplify HLA-B27 alleles); or
(3) residues 61–67 and/or residues 114–120 (which primers can be used to amplify HLA-Bw53 and HLA-B35 alleles);

which are all present in the alpha 1 or alpha 2 domain of HLA.

Preferred examples of the above primers have the sequences:

(1) 5'-CACTCCATGAGGTATTTC-3' (SEQ.ID: 1) and/or 5'-CCTCGCTCTGGTTGTAGTAGC-3' (SEQ.ID:2);
(2) 5'-CACTCCATGAGGTATTTC-3' (SEQ.ID:1) and/or 5'-CGGTCAGTCTGTGCCTT-3' (SEQ.ID:3); or
(3) 5'-CCGGAACACACAGATCTT-3' (SEQ.ID:4) and/or 5'-GTCGTAGGCGGACTGGTC-3' (SEQ.ID:5).

All of the five above primers have been unexpectedly found to amplify HLA sequences.

Particularly preferred primers are capable of selectively hybridizing to (and thus amplifying) a sequence:

(1) present in an HLA class I gene (such as type A, B or C, and preferably type B);
(2) present in an HLA-B27 gene; or
(3) present in an HLA-Bw53 and HLA-B35 gene or single alleles (e.g. HLA-B*2703).

Suitable primers include those that are capable of hybridizing to a nucleic acid sequence, or its complementary sequence, at least one of which encodes any or all of the following amino acid sequences:

1. HSMRYF (SEQ.ID:6) and/or YNQSEA (SEQ.ID:7);
2. HSMRYF (SEQ.ID:6) and/or CKAKAQ (SEQ.ID:8); or
3. DRNTQIF (SEQ.ID:9) and/or QSAYDG (SEQ.ID:10).

In this specification, apart from the sequence listing section, the single letter code will often be used to denote the amino acid, and for the sake of reference the single letter amino acid codes are as follows:

| Amino Acid | Three-letter Abbreviation | Single-letter Symbol |
|---|---|---|
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The primers used in the present application are thus suitably specific for (and thus the HLA sequence to be amplified is present in):

1. all alleles in a class (e.g. class I);
2. alleles only in a specific type (e.g. type B);
3. alleles only in a specific group, i.e. allele-group-specific (e.g. HLA-B27 group or the group containing HLA-Bw53 and HLA-B35); or
4. only one specific allele (e.g. HLA-B*2703).

Thus from the appropriate choice of primers, all alleles or only a chosen type, group or allele can be amplified. In this manner the present invention allows the typing of HLA alleles. It is preferred that the primers employed are either allele-group-specific or allele-specific. Particularly but not exclusively in the latter case, detection of and/or identification of an allele may be used in the diagnosis of disease or predisposition to disease.

The buffer suitably contains from 1% to 20%, preferably from 5 to 15% and optimally from 8 to 12%, of the polar aprotic solvent. Examples of such solvents include acetonitrile, DMF and acetone although the solvent of choice is dimethylsulphoxide (DMSO). The buffer also suitably contains an amount of each of the four deoxynucleotide triphosphates (dATP, dCTP, dGTP and dTTP) such as at a concentration of from 100 to 300 mM, preferably from 150 to 250 mM, and optimally from 180 to 220 mM. The primers are suitably provided in an amount of from 30 to 80, preferably from 40 to 60, pmol.

The buffer is suitably at a pH of from 6 to 10, optimally from 8.5 to 9.0. The same buffer is suitably employed for all stages (a) through to (d).

Alternatively or in addition the buffer preferably contains magnesium ions, for example supplied as magnesium chloride $MgCl_2$, such as in an amount of from 0.5 to 5 mM, preferably from 1 to 4 mM.

The buffer advantageously contains ammonium ions, such as provided by ammonium sulphate, which has surprisingly been found to assist amplification. The ammonium salt is suitably provided in an amount of from 10 to 50 mM, such as 15 to 30 mM, and optimally from 16 to 18 mM.

Advantageously the buffer will be provided with a chelating agent. The chelating agent assists amplification somewhat unexpectedly due to the fact that it may complex $MgCl_2$ which is often employed in the buffer. Indeed, EP-A-0258017 teaches that a chelating agent such as EDTA inactivates the polymerase. The chelating agent may be present in an amount of from 1 to 110 mM, preferably from 20 to 80 mM, and optimally from 60 to 70 mM. Preferred chelating agents include polyacetic acids, for example polyamine polyacetic acids such as ethylenediaminetetraacetic acid (EDTA).

It will be realised that the nucleic acid used in the process of the present application is suitably DNA, and preferably genomic DNA. The nucleic acid will generally be double-stranded. If it is, then it is preferred that the strands are separated by denaturation before or during stage (a).

Thus the double stranded nucleic acid can be suitably denatured by heating at a temperature of from 90°–110° C., such as at from 1 to 10 minutes. The same conditions are preferably employed in stage (c).

If a heat-stable polymerizing agent, such as Taq polymerase, is employed then stages (a) through to (d) may be performed simply by varying the temperature of the buffer, such as by using a thermal cycling apparatus.

In stage (b), the hybridizing (or annealing) of the oligonucleotide primers (there will usually be two), the temperature of the buffer can be particularly important. If the temperature is too low, the primers may anneal to many different sequences in the nucleic acid, resulting in non-specific amplification. Too high a temperature may result in insufficient hybridization and thus no amplification.

Stage (b) is preferably conducted at a temperature of from 41° to 70° C., preferably from 45° to 63° C., and optimally at from 50° to 58° C. The exact temperature employed may depend upon the primers being employed and other operating conditions. Thus, for the preferred primers whose specific sequences have been mentioned, the corresponding preferred temperature employed in stage (b) are as follows:

(1) from 45° to 55° C., preferably from 48° to 52° C. (SEQ.ID:1 and 2);

(2) from 47° to 57° C., preferably from 55° to 54° C. (SEQ.ID:1 and 3) ; and (3) from 53° to 63° C., preferably from 56° to 60° C. (SEQ.ID:4 and 5).

In stage (d), the temperature is suitably from 50° to 80° C. such as from 30 seconds to 2 minutes The invention finds particular use in the detection of, or detection of predisposition of, diseases or disorders including inflammatory arthropathy such as arthritis, and arthritis related diseases, including reactive arthritis, Reiter's syndrome, uveitis and in particular ankylosing spondylitis.

The process of the first aspect of the invention preferably additionally comprises:

(e) hybridizing a labelled oligonucleotide probe to the products of (d), that is to say hybridizing the probe to one of the HLA sequences in the primer extension products (or strands) produced during amplification.

One may then conduct the stage (f) of determining whether hybridization in (e) has occurred. The label is preferably a radioactive one, such as one containing $^{32}$P. This may be attached to the probe by using gamma $^{32}$P dATP (with T4 polynucleotide kinase).

Preferred probes are from 10 to 30 nucleotides in length, such as from 15 to 20 nucleotides. In addition, the probe is preferably specific for at least a portion of the alpha 1 domain of the HLA sequence, such as HLA type B.

Preferably the probe is a primer as mentioned before, and so the preferred features and characteristics of the primers are as for the probe mutatis mutandis. One may also use, as a probe, a nucleic acid sequence comprising, or substantially complementary to, a primer as described before.

Suitable probes are those that are specific for at least a portion of the nucleic acid corresponding to any of the following regions:

1. residues 70 to 90, such as 75 to 88, of the alpha 1 domain;

2. residues 50 to 80, such as 55 to 64 and/or 65 to 74 of the alpha 1 domain.

Particularly preferred probes have nucleic acid a sequence that comprises a sequence that is specific for a sequence that encodes $CX^1X^2KA$ wherein each of $X^1$ and $X^2$ individually represent any amino acid, or the complementary nucleic acid sequence. Such probes are suitably capable of hybridizing to nucleic acid corresponding to the 67–71, e.g. 66–72 region of the alpha 1 domain (HLA-B27 and thus specific only for the group) . Preferably $X^1$ represents K and/or $X^2$ represents A. A suitable probe is 5'-CTGCAAGGCCAAGGCACA-3' (SEQ.ID:11).

Other preferred probes have a sequence that is capable of hybridizing to a sequence spanning the sequence encoding residue 59 (H:His) in the alpha 1 domain (of HLA-B), e.g. residues 58 to 60, 57 to 61 or 56 to 62, such as one that encodes the polypeptide sequence GPEHWD (SEQ.ID:14). Such probes are suitable for identifying HLA-B*2703. A suitable probe is 5'-GGGCCGGAGCATTGGGAC- 3' (SEQ.ID:12).

A further suitable probe has a sequence that comprises a sequence that is specific for a sequence that encodes a Bw4 epitope, e.g. IALR, or the complementary nucleic acid sequence. A suitable probe is 5'-CGGATCGCGCTCCGC- TAC- 3' (SEQ.ID:13) .

The present invention thus encompasses a method of detecting and/or identifying an HLA sequence that may be indicative of a patient's susceptability to inflammatory arthropathy, such as ankylosing spondylitis, the method comprising amplifying nucleic acid by using the process of the first aspect of the present invention where the nucleic acid comprises an HLA sequence, such as a sequence from the alpha 1 domain, hybridizing to the HLA sequence a detectably labelled probe, and detecting any hybridized nucleic acid so formed.

The probe may be radio-labelled, metal labelled, or enzymatically labelled. The nucleic acid comprising the HLA sequence will generally be present in a sample, which sample is preferably obtained from DNA extracted from white blood cells. The detection of hybridization may thus indicate either the detection and/or identification of an HLA sequence and/or a specific type or sub-type of HLA sequence. In particular, the primer and/or probe may be specific for only one allele, for example HLA-B*2703. The detection and identification of this allele may indicate that a human is not susceptible to arthritis.

The present invention can therefore be thought of in another aspect as relating to a process for amplifying a human leucocyte antigen nucleic acid sequence, the sequence being contained in nucleic acid consisting of two complementary strands, which may be of equal or unequal length, the process comprising:

(a) hybridizing one oligonucleotide primer to each strand of nucleic acid;

(b) synthesising an extension product from each primer which is substantially complementary to the strand of nucleic acid to which the primer is hybridized, the synthesis being carried out in a buffer containing dimethylsulphoxide, the extension products being such that when they are separated from the complement, they can serve as a template for synthesis of an extension product of the other primer;

(c) separating the primer extension products from the templates on which they are synthesized to produce single stranded molecules; and (d) repeating (a) to (c) by synthesising primer extension products using the primers employed in (a) and each of the single stranded molecules that are produced in (c) as templates.

Stages (a) to (c) are repeated at least once, and preferably from 20 to 40, such as from 30 to 35, times.

A second aspect of the present invention relates to a kit for the detection and/or identification of a human leucocyte antigen (HLA) sequence (for example that may be indicative of the risk of a human being susceptible to inflammatory arthropathy, e.g. arthritis or an arthritis related disease) in a sample, the kit comprising:

(a) a container for an oligonucleotide primer for each strand of a nucleic acid sequence comprising the HLA sequence to be detected and/or identified, each primer being complementary, or substantially complementary, to a respective strand of each nucleic acid sequence from which an extension product can be synthesized, and when separated from its complement, can serve as a template for the synthesis of an extension product of the other primer;

(b) a container containing a polymerization agent;

(c) a container for each of four different nucleoside triphosphates;

(d) a container containing a buffer containing a polar aprotic solvent such as dimethylsulphoxide;

(e) a container containing a labelled oligonucleotide probe capable of hybridizing to the HLA sequence (if present in the sample); and (e) a container containing means for detecting hybridization of the probe to the HLA sequence.

Suitably the primer and/or the probe is specific for an allele group only (e.g. HLA-B27) or (preferably) specific for only one allele (e.g. HLA-B*2703). The kit may thus be used to determine the risk, such as a high or low risk, of a human to a disease or predisposition to disease. In particular, the kit can be used for determining whether a human has a high or low risk to inflammatory arthropathy, e.g. arthritis or an arthritis related disease (low risk may be indicated by the presence of the HLA-B*2703 allele).

Other preferred features and characteristics of the second aspect are as for the first aspect of the present invention mutatis mutandis.

A third aspect of the present invention relates to a nucleic acid sequence that is a primer or a probe as discussed for the first aspect.

A fourth aspect of the present invention relates to a method of detecting if a human has, or has predisposition to, a disease, for example being susceptible to a high or low risk inflammatory arthropathy, e.g. arthritis, such as ankylosing spondylitis, the method comprising conducting a process according to the first aspect and determining the presence of a HLA sequence indicative of a disease, or predisposition to a disease, such as inflammatory arthropathy.

Here inflammatory arthropathy includes rheumatic disease, arthritis such as osteoarthritis, rheumatoid arthritis, reactive arthritis, Reiter's syndrome, uveitis, ankylosing spondylitis, viral arthritis, psoriatic arthropathy, gouty arthritis, septic arthritis (suppurative arthritis), erythema nodosum and Henoch-Schloelein purpura.

Ankylosing spondylitis is often characterised by the gradual onset of low back pain (sometimes bilateral buttock pain) with morning stiffness. Peripheral joints may be affected. Often a reduced range of spinal movement and chest expansion is experienced, followed by rigidity of the spine, often in the cranial direction (firstly lumber, then dorsal, then cervical). Clinically one may often find high dorsal kyphosis, obliteration of lumber lordosis and flattening of the chest.

The method of the fourth aspect suitably involves isolating DNA from white blood cells before amplification according to the first aspect. The method also preferably involves the stages (e) and (f) of the first aspect. This is suitably conducted by dot blot analysis.

A fifth aspect of the present invention relates to a process for the preparation of a nucleic acid sequence of the third aspect, the process comprising coupling successive nucleotides together and/or ligating successive oligo- and/or polynucleotides together.

The nucleic acid (oligonucleotide probe and/or primer) is preferably made by chemical synthesis. For example, this may be achieved employing diethylphosphoramidites, and preferably using automated synthesis. The procedure suitably involves detritylation with trichloroacetic acid in dichloromethane, condensation with benzotriazole, and capping with acetic anhydride and dimethylamino pyridine in tetrahydrofuran and pyridine.

The invention will now be described by way of example only with reference to the following drawings:

BRIEF DESCRIPTION OF THE DRAWINGS

FIG. 1 shows the amino acid sequences of residues 1 to 90 of the alpha 1 domain of a number of HLA-B alleles;

FIG. 2 shows the amino acid sequences of residues 1 to 273 of the alpha 1 domain of a number of HLA-B alleles;

FIG. 4 shows the amino acid sequences of residues 1 to 90 of the alpha 1 domain of several HLA-B27 alleles, probes of the present invention that are specific for HLA-B*2703 and HLA-B27 group alleles and two primers of the present invention for amplification of HLA-B27 group alleles; and p FIG. 5 shows the results of dot blot analysis using the HLA-B27 detection probe.

Figure 3:
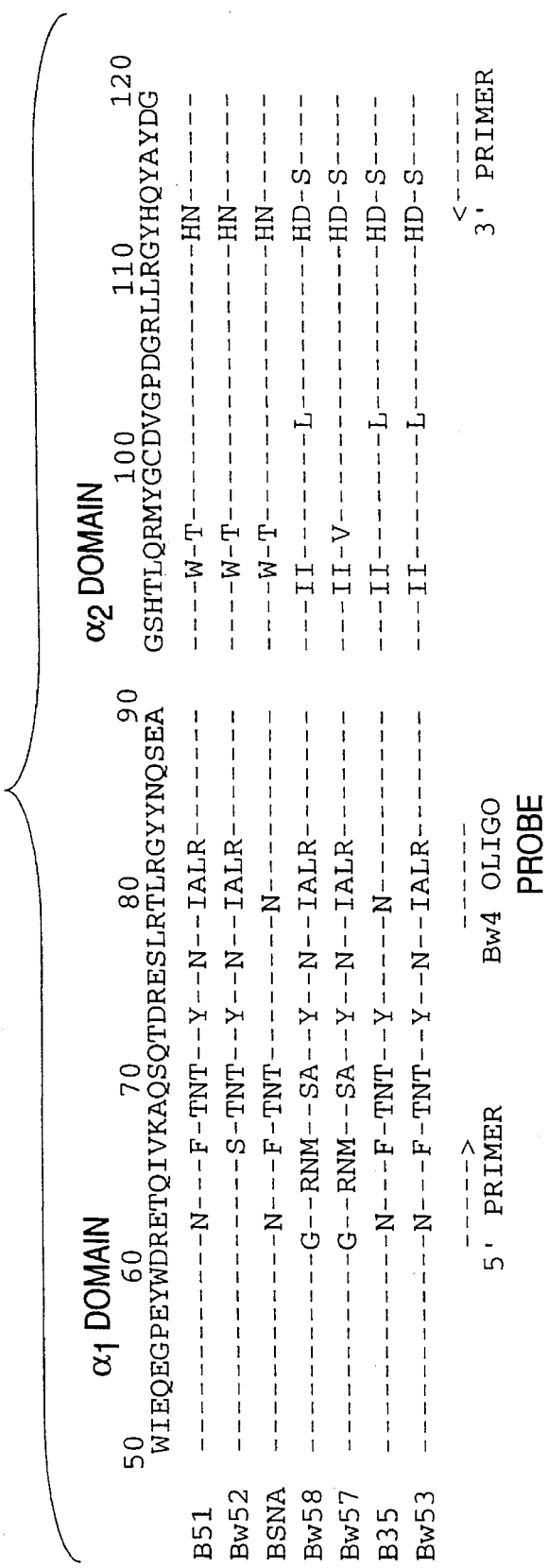
FIG. 3 shows the amino acid sequences of residues 50 to 120 of the alpha 1 domain of a number of HLA-B alleles and two primers, and one probe, of the present invention.

According to a sixth aspect of the present invention, there is provided a process for amplifying a nucleic acid sequence (which may or may not be hybridized), at least one strand coding for a human leucocyte antigen (HLA) sequence, the process comprising:

(a) hybridising one oligonucleotide primer to each strand of the nucleic acid sequence to be amplified, each primer being complementary or substantially complementary to a respective strand of the nucleic acid sequence;

(b) synthesising an extension product from each primer in a buffer containing a chelating agent and/or ammonium ($NH_4^+$) ions so that each extension product, when it is separated from its complement, can serve as a template for synthesis of an extension product of the other primer, at least one of the extension products comprising the HLA sequence;

(c) separating the primer extension products from their templates; and (d) synthesising primer extension products from the oligonucleotide primers used in (a) using the single strands produced in (c) as templates.

The chelating agent is preferably a polyacetic acid, such as a polyamine polyacetic acid. Particularly preferred is EDTA.

The buffer preferably contains magnesium ions which are suitably provided by means of a magnesium salt, for example magnesium chloride. Similarly, the source of ammonium ions may be provided by way of an ammonium salt, such as ammonium sulphate.

Preferred features and characteristics of the sixth aspect are as for the first aspect mutatis mutandis.

A seventh aspect of the present invention relates to a composition suitable for use as a buffer in a polymerase chain reaction amplification process, the composition comprising:

(a) an amount of each of the four nucleotide triphosphates;

(b) a source of magnesium ions; and (c) a chelating agent and/or a source of ammonium ($NH_4^+$) ions.

Preferred features and characteristics are as for the first and sixth aspects of the present invention mutatis mutandis.

The invention will now be described by way of example with reference to the accompanying Examples, which are not to be construed as being limiting, and which are provided for reasons of illustration only.

EXAMPLE 1

HLA Allele Amplification

The polymerase chain reaction and oligonucleotide hybridization was used to demonstrate that the predominant sub-type of HLA-B27 in the Gambia, West Africa is HLA-B*2703 which has never been found in other ethnic groups. This sub-type differs from the common Caucasian HLA-B27 sub-types in its recognition by cytotoxic T cells. Unlike other sub-types HLA-B*2703 has not been shown to be associated with ankylosing spondylitis and the predominance of this sub-type may in part account of the rarity of this condition in black populations.

712 Gambian adults and children where serotyped during a study of HLA alleles and childhood infections. 112 were healthy adult male blood donors and the 600 children were outpatients and inpatients with a variety of major and minor infections. No significant difference in frequency of HLA-B27 was seen between adults and children with different infections, so the frequency data were pooled.

A panel of 180 well-defined antisera were used to type either freshly isolated or cryopreserved peripheral blood lymphocytes (PBL) using the standard 2-stage NIH microcytotoxicity assay.

Following removal of peripheral blood lymphocytes, DNA was extracted from the residual white cells by lysis in a non-ionic detergent, overnight incubation in proteinase K and two phenol-chloroform extractions followed by one chloroform extraction. The DNA was precipitated in ethanol, redissolved in water and its concentration measured by spectrophotometric absorbance at 260 nm. For HLA-B27 typing oligonucleotide primers to conserve sequences at either end of the exon encoding the alpha 1 domain of HLA class I sequences were used (see FIG. 4). The primers used were:

5'-CACTCCATGAGGTATTTTC-3' (SEQ.ID:1) and

5'-CCTCGCTCTGGTTGTAGTAGC-3' (SEQ.ID:2) (see FIG. 4).

The primers were synthesized using the procedure of Beaucage and Caruthers, *Tetrahedron Letters* 24: 245 (1981). Amplification was performed in a buffer containing 3 mM $MgCl_2$, 17 mM ammonium sulphate, 66 mM Tris of pH 8.8, 67 mM EDTA, 10% DMSO, 1 mM spermidine, 200 microM of each dNTP with 50 pmol of each primer and 0.5 mcg of DNA in a 50 microliter reaction volume. Samples were denatured for 10 minutes at 100° C., 0.2 units of AMPLITAQ (Trade Mark, Taq polymerase available from Cetus Corporation, 1400 53rd Street, Emeryville, Calif. 946078, U.S.A.) added and 30 cycles performed of 90 seconds at 94° C., 60 seconds at 50° C. (annealing), 10 seconds at 60° C. and 60 seconds at 72° C. using a thermal cycler. (CEP Scientific PREM III model, available from CEP Scientific Limited, Sunrise Parkway, Linford Wood, Milton Keyes, MK14 6QF, England).

EXAMPLE 2

Allele-group-specific Amplification

The procedure of Example 1 was followed except that for allele-specific HLA-B27 group amplification the same first 5' primer was used (SEQ.ID:1) with the 3' primer 5'-CGGTCAGTCTGTGCCTT-3' (SEQ.ID:3), (see FIG. 4) with 1 mM magnesium chloride in the amplification buffer, annealing at 52° C., and the product detected by ethidium bromide staining following agarose gel electrophoresis and visualisation of a band of 210 base pairs in size. It was found that the use of a polar aprotic solvent such as DMSO in the reaction mix was essential for successful amplification, probably because the high GC nucleotide content of HLA class I sequences leads to amplification-refractory DNA secondary structures in its absence.

EXAMPLE. 3

Allele-group-specific Amplification

The procedure of Example 1 was conducted except using the primers 5'-CCGGAACACACAGATCTT-3' (SEQ.ID:4) and 5'-GTCGTAGGCGGACTGGTC-3' (SEQ.ID:5) (see FIG. 3) for allele-group-specific amplification of HLA-Bw55 and HLA-B35 alleles. The same procedure of Example 1 was conducted except that the magnesium chloride was provided at a concentration of 1 mM and 35 cycles were performed of 90 seconds at 94° C., 120 seconds at 58° C. (to anneal) and 120 seconds at 72° C.

EXAMPLES 4–6

Detection of HLA Alleles 10 microliters of the reaction product from amplification in Examples 1 to 3 were either dotted onto nitrocellulose using a manifold baked at 80° C. for 2 hours (for B27 alleles) or electrophoresed on 1.5% agarose gels before Southern transfer on to a nitrocellulose filter and baking at 80° C. for 2 hours. Prehybridisation (using 1.8×SSC, standardised sodium citrate, 10×Denhardts solution, 2 mg/ml salmon sperm DNA and 0.2% SDS) and hybridisation (using 1.8× SSC with 0.1% SDS) were performed at 31° C. using end-labelled oligonucleotides using T4 polynucleotide kinase and the radioactive label gamma-$^{32}$P-ATP. The probes used were:

(Example 4) B27; 5'-CTGCAAGGCCAAGGCACA-3' (SEQ.ID:11) (washing temperature 58° C.);

(Example 5) B*2703; 5'-GGGCCGGAGCATTGGGAC-3' (SEQ.ID:12) (washing temperature 63° C.); and (Example 6) Bw4; 5'-CGGATCGCGCTCCGCTAC-3' (SEQ.ID:13) (washing temperature 59° C.) (see FIGS. 3 and 4).

These were synthesized usign the procedure of Beaucage and Caruthers, supra. Filters were washed in 6 times SSC at the stated temperatures for 20 minutes and autoradiographed for 2–12 hours. .

The results of the dot blot analysis using a HLA-B27 group specific probe is given in FIG. 5. Position 1 represents a cloned negative control (HLA-Bw53), position 2 a cloned HLA-B27 allele. Samples in positions 9, 14, 15 and 24 were amplified from individuals who did not have HLA-B27 on serological typing. All other samples were taken from HLA-B27 carriers.

Of the 712 Gambians that were typed serologically 18 were found to be carriers of HLA-B27, 2.6%. This is a lower frequency than found in a small survey in Mali (9.7%) but higher than in Nigerians and South African blacks amongst whom HLA-B27 is apparently very rare. Using amplification primers to conserved sequences at the ends of exon 2 the sequence encoding the alpha 1 domain of class I alleles (including HLA-A, -B and -C) was amplified (FIG. 4). Inspection of the sequences of 88 class I alleles showed that amino acids 67–71 are unique to HLA-B27. An oligonucleotide probe to the nucleotide sequence encoding these residues hybridized to amplified DNA from all 18 individuals with HLA-B27 (FIG. 5) but none of the 30 controls who between them typed for 47 different class I alleles. Hence this oligonucleotide appears to be completely specific for HLA-B27. Using a 3' amplification primer specific to the residues encoded by the B27-specific detection oligonucleotide only HLA-B27 positive samples were amplified (data not included), providing an alternative diagnostic method.

The HLA sub-type HLA-B2703 has been reported in a single American black. To look for this sequence in the Gambia an oligonucleotide which spans amino acid 59 of the-alpha 1 domain was synthesized, which is the only position at which HLA-B*2703 differs from the most common Caucasian HLA-B27 allele, HLA-B*2705 (FIG. 4). Surprisingly, it was found that 11 of the 18 HLA-B27 positive samples from the Gambia hybridized to this oligonucleotide. All non-HLA-B27 controls did not.

Not all HLA class I alleles have unique sequences which will allow their detection by a single oligonucleotide probe. Many are composed of patchwork type sequences where a combination of sequence motifs defines the allelic type. For example, the common African allele HLA-Bw53 differs from another common allele, HLA B35, only by the presence of a short sequence at the 3' end of exon 2 that is shared by many other alleles, and which specifies the serological Bw4 epitope. However, in principle, all of these alleles can also be typed using PCR by employing specific amplification primers. These are chosen so as to amplify only a single sequence (allele-specific amplification) or a group of sequences (allele-group-specific amplification) that can then be distinguished by oligonucleotide hybridization. As an example of the feasibility of this latter approach for HLA class I typing specific primers were used to amplify only HLA-Bw53 and HLA-B35 from over 100 Gambians with these alleles and selectively detected HLA-Bw 53 with a Bw4-specific oligonucleotide, obtaining results completely concordant with the serological types.

The rarity of HLA-B27 associated diseases in sub-Saharan Africa has been thought to be related to the near absence of this HLA type in unmixed Africans. This is not the case in the Gambia where nearly 3% of the population carry HLA-B27. An alternative and attractive explanation raised by this study is that the African sub-type of HLA-B27, B*2703, carries a lesser risk of ankylosing spondylitis and other HLA-B27 related conditions. Previously HLA-B*2703 has only been identified previously in one healthy American black. Four of the other 5 sub-types of HLA-B27 have been shown to be associated with ankylosing spondylitis.

Two observations are consistant with this. Firstly, T lymphocytes that respond to the common sub-types HLA-B* 2703 and HLA-B*2702 in both alloreactive and peptide specific cytotoxic T cell (CTL) assays fail to recognise HLA-B*2703. This would be predicted by the model of HLA-B27 disease pathogenesis which implicates cytotoxic lymphocytes reactive with an HLA-B27 specific peptide carried by foreign pathogens that crossreact with a similar or identical peptide normally expressed in joint tissues, the "arthritogenic peptide" model of ankylosing spondylitis and reactive arthritis. Secondly, the limited data available on American blacks with ankylosing spondylitis suggest that they have a lower relative risk of disease than Caucasians when they are carriers of HLA-B27. A lower carrier rate for HLA-B27 should not reduce the observed relative risk, but the presence of a common HLA-B27 sub-type conferring lesser susceptibility would do so.

The importance of determining whether or not HLA-B*2703 is associated with a high risk of ankylosing spondylitis arises from the single amino acid difference between this allele and the common Caucasian sub-type HLA-B*2705, a substitution of histidine for tyrosine at position 59 of the alpha 1 domain (FIG. 4). If the former is not a susceptibility allele this would strongly support an arthritogenic peptide model of disease pathogenesis rather than the "altered-self" and "molecular mimicry" models which propose a crucial role for the cysteine residue at position 71 or neigbouring residues. Furthermore, it would provide a potential method of screening peptides isolated from microorganisms which represent HLA-B27 epitopes for possible involvement in disease pathogenesis.

The HLA-B27 typing and sub-typing of numerous blacks with HLA-B27 related diseases may define the risk of disease associated with HLA-B*2703. The availability of a simple method of HLA class I typing and sub-typing may facilitate such studies.

I claim:

1. A process for amplifying by the polymerase chain reaction a human leukocyte antigen nucleic acid sequence comprising a primer pair selected from the group consisting of Sequence I.D. No. 1–5, the process comprising:
   (a) hybridizing one oligonucleotide primer to each strand of the nucleic acid sequence to be amplified, each primer being complementary to a respective strand of the nucleic acid sequence;
   (b) synthesizing an extension product from each primer in a buffer containing a polar aprotic solvent at a concentration of 5 to 15% so that each extension product, when it is separated from its complement, can serve as a template for synthesis of an extension product of the other primer, at least one of the extension products comprising the HLA sequence;
   (c) separating the primer extension products from their templates; and
   (d) synthesizing primer extension products from the oligonucleotide primers used in (a) using the single strands produced in (c) as templates.

2. A process as claimed in claim 1 wherein the polar aprotic solvent is DMSO.

3. A process as claimed in claim 1 wherein the polar aprotic solvent DMSO is provided at a concentration of from 5 to 15%.

4. A process as claimed in claim 1 wherein the buffer is provided with EDTA.

5. A process as claimed in claim 1 wherein the nucleic acid sequence to be amplified is genomic DNA.

6. A process as claimed in claim 1 wherein stage (b) is conducted at a temperature of from 41° to 70° C.

7. A kit for the detection or identification by the polymerase chain reaction of a human leukocyte antigen (HLA) sequence in a sample, the kit comprising:

(a) a container comprising oligonucleotide primers selected from the group consisting of sequence I.D. Nos. 1–5;

(b) a container containing a DNA or RNA polymerase;

(c) a container for each of four different nucleoside triphosphates;

(d) a container containing a PCR buffer containing a polar aprotic solvent at a concentration of 5 to 15%;

(e) a container containing a labelled oligonucleotide probe selected from the group consisting of Sequence I.D. Nos. 11–13.

8. A process for amplifying a nucleic acid sequence as claimed in claim 1 comprising two primers for a class I human leucocyte antigen (HLA) sequence, the process comprising:

(a) hybridising one oligonucleotide primer to each strand of the class I HLA nucleic acid sequence to be amplified, each primer being complementary to a respective strand of the nucleic acid sequence;

(b) synthesising an extension product from each primer in a buffer containing EDTA or ammonium ($NH_4^+$) ions so that each extension product, when it is separated from its complement, can serve as a template for synthesis of an extension product of the other primer, at least one of the extension products comprising the HLA sequence;

(c) separating the primer extension products from their templates; and (d) synthesising primer extension products from the oligonucleotide primers used in (a) using the single strands produced in (c) as templates.

9. Nucleic acid primers selected from the group consisting of Sequence I.D. Nos. 1–5.

10. Nucleic acid probes selected from the group consisting of Sequence I.D. Nos. 11–13.

* * * * *

SEQUENCE LISTING ( 1 ) GENERAL INFORMATION:

( i i i ) NUMBER OF SEQUENCES: 14

( 2 ) INFORMATION FOR SEQ ID NO: 1:

( i ) SEQUENCE CHARACTERISTICS:
        ( A ) LENGTH: 18 base pairs ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..18

( x i ) SEQUENCE DESCRIPTION: SEQ ID NO: 1:

```
CAC  TCC  ATG  AGG  TAT  TTC                                                    18
His  Ser  Met  Arg  Tyr  Phe
 1                    5
```

( 2 ) INFORMATION FOR SEQ ID NO: 2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 2:

```
CCTCGCTCTG  GTTGTAGTAG  C                                                       21
```

( 2 ) INFORMATION FOR SEQ ID NO: 3:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 3:

```
CGGTCAGTCT  GTGCCTT                                                             17
```

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..18

( x i ) SEQUENCE DESCRIPTION: SEQ ID NO: 4:

```
CCG  GAA  CAC  ACA  GAT  CTT                                                    18
Asp  Arg  Asn  Thr  Gln  Ile
 1                    5
```

( 2 ) INFORMATION FOR SEQ ID NO: 5:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 5:

GTCGTAGGCG GACTGGTC

18

( 2 ) INFORMATION FOR SEQ ID NO: 6:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 6:

His Ser Met Arg Tyr Phe
1               5

( 2 ) INFORMATION FOR SEQ ID NO:7:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 7:

Tyr Asn Gln Ser Glu Ala
1               5

( 2 ) INFORMATION FOR SEQ ID NO: 8:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 8:

Cys Lys Ala Lys Ala Gln
1               5

( 2 ) INFORMATION FOR SEQ ID NO: 9:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 9:

Asp Arg Asn Thr Gln Ile Phe
1               5

( 2 ) INFORMATION FOR SEQ ID NO:10:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 10:

Gln Ser Ala Tyr Asp Gly
1               5

( 2 ) INFORMATION FOR SEQ ID NO: 11:

( i ) SEQUENCE CHARACTERISTICS:
   ( A ) LENGTH: 18 base pairs
   ( B ) TYPE: nucleic acid
   ( C ) STRANDEDNESS: single
   ( D ) TOPOLOGY: linear ( i i ) MOLECULE TYPE: DNA (genomic)

( x i ) SEQUENCE DESCRIPTION: SEQ ID NO: 11:

CTGCAAGGCC AAGGCACA                                                                                     18

( 2 ) INFORMATION FOR SEQ ID NO: 12:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: DNA (genomic)

( i x ) FEATURE:
      ( A ) NAME/KEY: CDS
      ( B ) LOCATION: 1..18

( x i ) SEQUENCE DESCRIPTION: SEQ ID NO: 12:

GGG  CCG  GAG  CAT  TGG  GAC                                                                            18
Gly  Pro  Glu  His  Trp  Asp
 1                    5

( 2 ) INFORMATION FOR SEQ ID NO:13:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO: 13:

CGGATCGCGC TCCGCTAC                                                                                     18

( 2 ) INFORMATION FOR SEQ ID NO: 14:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: protein ( x i ) SEQUENCE DESCRIPTION: SEQ ID NO: 14:

Gly  Pro  Glu  His  Trp  Asp
    1                    5